US00PP13871P29

(12) United States Plant Patent

Janick et al.

(10) Patent No.: US PP13,871 P2

(45) Date of Patent: Jun. 10, 2003

(54) APPLE TREE NAMED 'CO-OP 33'

(75) Inventors: Jules Janick, West Lafayette, IN (US); Edwin B. Williams, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/028,784

(22) Filed: Dec. 21, 2001

(51) Int. Cl.[7] ..... A01H 5/00

(52) U.S. Cl. ..... Plt./161

(58) Field of Search ..... Plt./161

(56) References Cited

U.S. PATENT DOCUMENTS

PP12,323 P2 * 1/2002 Janick et al. ..... Plt./161

OTHER PUBLICATIONS

Internet web pages, "Pedigree, A Genetic Resource Inventory System," http://www.universaldbase.com/pgris/pedigree/1stapp.html, originally found on web site on Sep. 6, 2002, pp. 1–5.*

* cited by examiner

*Primary Examiner*—Bruce R. Campell
*Assistant Examiner*—Susan B. McCormick
(74) *Attorney, Agent, or Firm*—Klarquist Sparkman, LLP

(57) ABSTRACT

A new apple variety of distinguished by a small size fruit; resistance to apple scab; fruit having extremely crisp flesh and excellent flavor; and fruit that ripens in mid-September, but does not readily fall from the tree.

1 Drawing Sheet

CROSS REFERENCE TO RELATED APPLICATIONS

None.

STATEMENT REGARDING FEDERALLY SPONSORED RESEARCH OR DEVELOPMENT

None.

Latin Name of the Genus and Species of the Plant Claimed: *Malus×domestica.*

Variety Denomination: 'Co-op 33'.

BACKGROUND OF THE INVENTION

The present invention relates to a new and distinct variety of apple tree named 'Co-op 33'. Our new tree resulted from a planned hybridization program and is a selection from crossing 'PCF2-134' (a proprietary, unpatented apple tree) as the seed parent with '669 N.J.5' (a proprietary, unpatented apple tree) as the pollen parent. The resulting tree was selected when growing in a cultivated area of Purdue University in West Lafayette, Ind.

BRIEF SUMMARY OF THE INVENTION

The 'Co-op 33' variety is distinguished from other apple varieties due to the following unique combination of characteristics: resistance to apple scab; fruit has extremely crisp flesh and excellent flavor; fruit does not drop when ripe; small size; and ripens in mid-September, when grown in Lafayette, Ind.

Asexual reproduction of this new variety has been accomplished by grafting and budding onto rootstocks 'Malling 7' (unpatented) and 'Malling Merton 111' (unpatented) rootstocks shows that the foregoing characteristics come true to form, are firmly fixed, and are established and transmitted through succeeding propagations.

The original tree and progeny have been observed growing in a cultivated area of Purdue University in West Lafayette, Ind. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWING

The accompanying illustration shows typical fruit and leaf specimens of this new variety.

The colors of an illustration of this type may vary with lighting conditions and, therefore, color characteristics of this new variety should be determined with reference to the observations described herein, rather than from this illustration alone.

DETAILED BOTANICAL DESCRIPTION

The following detailed description of the 'Co-op 33' variety is based on observations of asexually reproduced progeny. The observed progeny were trees which were 17 years of age growing on 'Malling 7' rootstock in West Lafayette, Ind.

Scientific name: *Malus×domestica* 'Co-op 33'.

Parentage:

*Seed parent.*—'PCF2-134' (unpatented).

*Pollen parent.*—'669 N.J. 5' (unpatented), a variety that resulted from a cross between 'Crandall' (unpatented) and 'PRI 14-226' (unpatented).

Tree:

*Vigor.*—Moderate.

*Overall shape.*—Spreading.

*Height.*—From about 10 to about 12 feet.

*Width.*—Overall spread of about 12 feet.

*Caliper.*—About 5.8 inches at 15 inches above ground.

*Trunk.*—Stocky.

*Trunk bark texture.*—Rough and scaly.

*Trunk bark color.*—Grey (RHS 201A), with round to elongated lenticels, typical examples of which measured about 0.46 to about 0.64 inches. The lenticels were green to grey-orange (RHS 143 to RHS 167D) in color.

*Primary branches.*—Spreading, emerging from the trunk at an angle of about 45 to about 55 degrees along the entire height of the tree.

*Branch color.*—Varies with age; observed one-year old branches were grey-purple (RHS 183A) in color, while two-year old branches were grey-brown (RHS 199B) in color.

*Branch pubescence.*—New wood exhibits branch pubescence, while older wood does not.

*Branch lenticels.*—Medium density (about 50 per square inch), oval, about 0.04 inch long, white (RHS N155A) in color.

*Bearing.*—Annual bearing, though some tendency toward biennial bearing has been observed if trees are over-cropped.

*Hardiness.*—Zone 5, comparable to 'Golden Delicious'.

*Disease and insect resistance.*—Resistant to apple scab; moderately resistant to powdery mildew, fireblight, and frogeye leaf spot; slightly susceptible to apple maggot; susceptible to cedar-apple rust.

Leaves:

*Texture.*—Smooth, Moderately thick.

*Sheen.*—Dull.

*Length.*—About 2.6 inches to about 3.8 inches, averaging about 3.1 inches.

*Width.*—About 1.3 inch to about 1.8 inch, averaging about 1.6 inch.

*Thickness.*—About 0.004 inch to about 0.02 inch, averaging about 0.01 inches.

*Petiole.*—Length of about 1.2 inch long and about 0.06 inch in diameter; yellow-green in color (RHS 146A), pubescent.

*Margin.*—Serrate.

*Tip shape.*—Acute.

*Stipules.*—Needle-shaped; two in number, with opposite arrangement; yellow-green (RHS 154B) in color; and 0.007 inch in diameter.

*Leaf color.*—Upper leaf surface: Yellow-green (RHS 147A). Lower leaf surface: Yellow-green (RHS 148A). Vein: Yellow-green (RHS 154A).

*Pubescence.*—Upper leaf surface is non-pubescent. Lower leaf surface has some white pubescence. The length, width, thickness and other measurements were obtained from observations of ten typical leaves in September of 2001.

Flowers:

*Size.*—Medium, approximately 46 to 51 mm in diameter.

*Shape.*—Ovoid to round.

*Color.*—Unopened bud: red-purple in color (RHS N57B to 62D). Opened flower: Petal color is white, (RHS N155A), on both sides.

*Petals.*—Five petals per flower; each petal is ovoid to round in shape, typically 17 to 24 mm long.

*Bud length* (*expanded pink*).—10.2 mm.

*Bud diameter* (*tight pink*).—7 mm.

*Petal shape.*—Base: slightly acuminate; Apex: rounded.

*Stamen.*—Twenty per flower; each stamen is 8 to 9 mm long and white in color. Arranged in a single row.

*Anthers.*—Yellow-orange (RHS 17C) in color.

*Pistil.*—Stigma: About 10 mm long. Style: Five in number, fused at base fused; yellow-green (RHS 150D) in color.

*Sepals.*—About 7 mm long and 2 mm wide; recurved and not touching; green (RHS 142C) in color, tinged at tip with red purple (RHS 68B); pubescent.

*Pollen.*—Yellow-orange (RHS 17C) in color.

*Fragrance.*—Slight.

Pedicel:

*Length.*—18.0 mm.

*Diameter.*—1.5 mm. Color is green (RHS 142C).

Fruit: (Observations from a limited number of fruit in September of 2001.).

*Shape.*—Round-oblate; symmetrical with a length to diameter ratio of typically between 0.8 and 0.9; no ribbing and no lobes at calyx end.

*Size.*—Small, about 2.2 to 2.5 inches long and 2.6 to 2.9 inches in diameter.

*Cavity.*—Typically between 0.9 inch and 1.0 inch deep and between 0.35 and 0.4 inch wide.

*Basin.*—Medium width and depth, typically between 0.4 and 0.45 inch deep and about 0.95 inch wide; pubescence on calyx.

*Stem.*—Medium length, typically of about 0.85 inch and about 0.08 inch in diameter; red-purple (RHS 61A) in color.

*Locules.*—Five, small, closed locules; seeds are free from the carpel wall at maturity.

*Skin.*—Thin and glossy, with no tendency to become waxy or oily in storage.

*Lenticels.*—Inconspicuous, round and red-purple (RHS 61C) in color.

*General color effect.*—Washed; green-yellow to yellow with a red-purple over color. Ground color: Yellow-green (RHS 149), persisting in the basin; ground color changes toward yellow during the time from first to last picking. Overcolor: Red-purple (RHS 61A to 61B) with 90% to 100% coverage at maturity. Russet: No russeting observed.

*Fruit characteristics at maturity* (*based on five fruit tested in September of 2001*).—Acid content: About 0.3 g/100 ml % malic acid. Firmness: About 7.5 kg to about 10.0 kg, averaging about 8.6 kg. Soluble solids: About 11.9% to about 12.6%, averaging about 12.3%. Starch index: On a scale of 1 (high starch) to 9 (low starch), range 8 to 9 starch index. Flavor: Rich flavor, complex mixture of sweet and tart. Juiciness: Juicy. Flesh color: Yellow-white (RHS 158A). Aroma: Slight.

*Core.*—Basal bundle area shape. Width: About 0.87 inches. Length: About 0.98 inches. Calyx tube: Closed and about 0.20 inches long. Core lines: Weakly defined.

*Seed.*—About 1 to 2 seeds per cell; acute shape, measuring about 0.34 inches long and 0.19 inches wide; grey-orange (RHS 166A) in color.

*Fruit production.*—First picking date in 2001 was about September 12, and last picking date was about September 18. Fruit hangs well on the tree and can be picked into October; average production is 160 lbs. of fruit per tree.

*Keeping quality.*—Fruit remains fresh for about two weeks at room temperature. Fruit in storage has been observed to maintain its quality for up to about two months in cold storage (34° F.). The maximum time that fruit quality can be maintained in cold storage is unknown.

*Usage.*—Particularly good for eating; tree is suitable for home gardening.

*Fruit weight.*—(Based on a single fruit with a 2.9 inch diameter×2.5 inch height tested in October 2002) 172 g.

I claim:

1. A new and distinct variety of apple tree, substantially as herein shown and described.

* * * * *

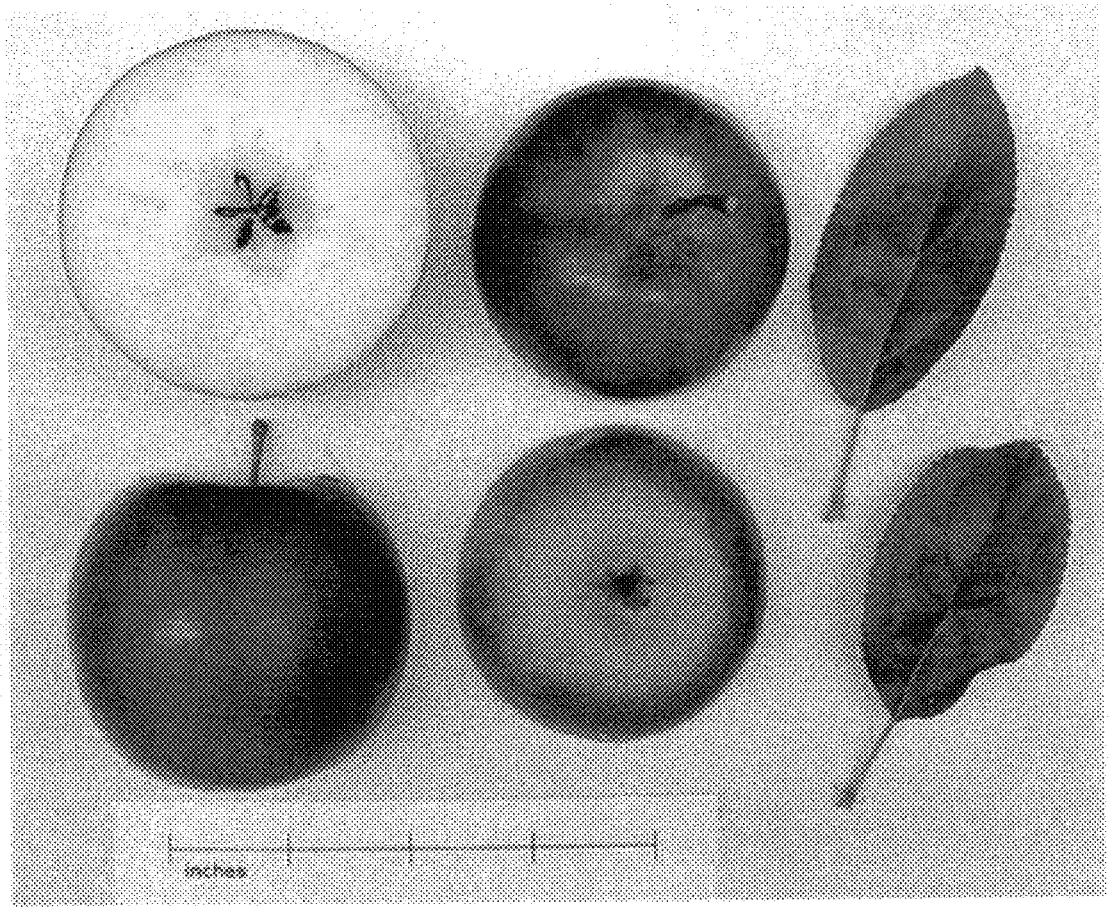
inches

UNITED STATES PATENT AND TRADEMARK OFFICE
Certificate

Patent No. PP 13,871 P2 Patented: June 10, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jules Janick, West Lafayette, IN (US); Edwin B. Williams, Lafayette, IN (US); Joseph C. Goffreda, Millstone Township, NJ (US); and Schuyler S. Korban, Champaign, IL (US).

Signed and Sealed this Fifth Day of September 2006.

ANNE MARIE GRUNBERG
*Supervisory Patent Examiner*
Art Unit 1661